(12) United States Patent
Dickson

(10) Patent No.: US 12,064,164 B2
(45) Date of Patent: Aug. 20, 2024

(54) ELECTROSURGICAL INSTRUMENT

(71) Applicant: GYRUS MEDICAL LIMITED, Cardiff (GB)

(72) Inventor: James Alan Dickson, Cardiff (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 291 days.

(21) Appl. No.: 17/391,133

(22) Filed: Aug. 2, 2021

(65) Prior Publication Data

US 2022/0061910 A1  Mar. 3, 2022

(30) Foreign Application Priority Data

Aug. 26, 2020 (GB) ..................................... 2013367

(51) Int. Cl.
*A61B 18/14* (2006.01)
*A61B 18/12* (2006.01)
(Continued)

(52) U.S. Cl.
CPC ...... *A61B 18/1402* (2013.01); *A61B 18/1206* (2013.01); *A61B 18/14* (2013.01); *A61B 18/148* (2013.01); *A61B 17/32002* (2013.01); *A61B 2018/00083* (2013.01); *A61B 2018/00136* (2013.01); *A61B 2018/00142* (2013.01); *A61B 2018/00178* (2013.01); *A61B 2018/00202* (2013.01); *A61B 2018/00208* (2013.01); *A61B 2018/00577* (2013.01); *A61B 2018/00589* (2013.01); *A61B 2018/00601* (2013.01); *A61B 2018/00607* (2013.01);
(Continued)

(58) Field of Classification Search
CPC ........ A61B 18/148; A61B 2018/00208; A61B 2218/007; A61B 2217/005
See application file for complete search history.

(56) References Cited

U.S. PATENT DOCUMENTS 7,150,747 B1  12/2006  McDonald et al.
2003/0163126 A1  8/2003  West
(Continued)

FOREIGN PATENT DOCUMENTS

GB  2477354 A  8/2011
GB  2552682 A  2/2018
(Continued)

OTHER PUBLICATIONS

Oct. 25, 2022 Office Action issued in Japanese Patent Application No. 2021-126495.
(Continued)

*Primary Examiner* — Sean W Collins
(74) *Attorney, Agent, or Firm* — Oliff PLC

(57) ABSTRACT

An electrosurgical instrument end effector includes an active electrode received by an insulating material, the active electrode including a primary suction aperture which provides access to a primary fluid channel extending from the active electrode, through the insulating material, to a lumen. The lumen is arranged to carry fluid to and from a surgical site when in use. The end effector further includes at least one additional fluid channel providing alternative access to the primary fluid channel from the active electrode, wherein the at least one additional fluid channel bypasses the primary suction aperture.

20 Claims, 8 Drawing Sheets

(51) Int. Cl.
  *A61B 17/32*    (2006.01)
  *A61B 18/00*    (2006.01)
(52) U.S. Cl.
  CPC .............. *A61B 2018/00916* (2013.01); *A61B 2018/126* (2013.01); *A61B 2018/1467* (2013.01); *A61B 2018/1497* (2013.01); *A61B 2218/007* (2013.01)

(56) References Cited

U.S. PATENT DOCUMENTS

| | | |
|---|---|---|
| 2009/0048592 A1* | 2/2009 | Thomas .............. A61B 18/148 606/41 |
| 2010/0121321 A1 | 5/2010 | Ryan |
| 2014/0257277 A1* | 9/2014 | Woloszko ........... A61B 18/148 606/41 |
| 2014/0276704 A1 | 9/2014 | McKay |
| 2014/0316401 A1 | 10/2014 | Crews et al. |
| 2015/0051628 A1 | 2/2015 | Schoeler et al. |
| 2015/0265337 A1 | 9/2015 | Bloom |
| 2017/0224368 A1 | 8/2017 | Germain et al. |
| 2019/0008538 A1 | 1/2019 | Germain et al. |
| 2019/0059983 A1 | 2/2019 | Germain et al. |
| 2019/0328417 A1 | 10/2019 | Germain |
| 2019/0374278 A1 | 12/2019 | Malkevich et al. |
| 2019/0380774 A1 | 12/2019 | Hayes et al. |
| 2022/0015822 A1 | 1/2022 | Brockmann |
| 2022/0160425 A1* | 5/2022 | Doll .................... A61B 18/148 |

FOREIGN PATENT DOCUMENTS

| | | |
|---|---|---|
| JP | 2010-535539 A | 11/2010 |
| JP | 2022-522118 A | 4/2022 |
| WO | 2009/019426 A1 | 2/2009 |
| WO | 2013/191811 A1 | 12/2013 |
| WO | 2017/034863 A1 | 3/2017 |
| WO | 2017/180423 A1 | 10/2017 |
| WO | 2018/213465 A1 | 11/2018 |
| WO | 2020/172659 A1 | 8/2020 |

OTHER PUBLICATIONS

Jul. 4, 2023 Office Action issued in Japanese Patent Application No. 2021-137135.
Feb. 7, 2023 Office Action issued in Japanese Patent Application No. 2021-126495.
Jan. 10, 2023 Office Action issued in Japanese Patent Application No. 2021-137135.
Feb. 18, 2021 Search Report issued in British Patent Application No. GB2014541.3.
Jun. 11, 2021 Search Report issued in British Patent Application No. GB2014541.3.
Feb. 5, 2021 Search Report issued in British Patent Application No. 2013367.4.
Sep. 19, 2023 Office Action issued in U.S. Appl. No. 17/408,560.
Apr. 8, 2024 Office Action issued in GB Patent Application No. GB2013367.4.

* cited by examiner

ELECTROSURGICAL INSTRUMENT

TECHNICAL FIELD

The present invention relates to suction flow paths in electrosurgical instruments. More specifically, the present invention relates to peripheral suction flow paths located in end effectors of electrosurgical instruments.

BACKGROUND TO THE INVENTION AND PRIOR ART

Surgical instruments, including radio frequency (RF) electrosurgical instruments, have become widely used in surgical procedures where access to the surgical site is restricted to a narrow passage, for example, in minimally invasive "keyhole" surgeries.

A number of legacy wet-field RF hand instruments for arthroscopy use a saline suction pathway at the distal tip during either ablating or coagulating tissue. In general terms, suction and peripheral suction provide the following benefits:
  (i) Cools the RF tip by drawing colder saline over the hot RF tip during use;
  (ii) Helps to remove ablated tissue debris from surgical site;
  (iii) Multiple flow pathways (primary and peripheral) help to maintain a flow of saline during blockage instances, or if the face of the tip is compressed into tissue;
  (iv) Removes bubbles to improve joint visibility; and
  (v) Positive effect on the formation of plasma at the tip.

Recent legacy RF tip designs generally have multiple flow pathways which are categorised as either primary or peripheral suction. The primary suction pathway is generally one or more holes in the tissue contacting flat portion of the tip. These holes tend to be larger by design, but are blocked with tissue as soon as the face of the tip is buried into the surface of target tissue, so can easily be blocked. The peripheral suction consists of one or more pathways which provide suction around the peripheral edge of the RF tip which are not so easily blocked by target tissue.

The concept of a peripheral suction flow path is incorporated into a number of legacy devices. For example, see WO 2009/019426 which describes an electrosurgical instrument having a primary suction aperture (14a) and a gap (25) between the active electrode (14) and the insulation member (16) which forms an additional suction channel. However, the peripheral suction channel of WO 2009/019426 is a gap between the insulating member and the active electrode, and provides a direct path to the suction lumen (22), without going via the primary suction channel connecting the primary suction aperture (14a) to the suction lumen (22). If this configuration were implemented into an opposite sided RF shaver instrument, it would result in substantially decreased suction pressure when using the shave function and negatively affect the preferential RF tracking, as described in more detail below.

The difference between the 'primary' suction flow and the peripheral suction path is that the peripheral suction is typically around the perimeter of the tip, and draws saline through from the sides/underneath. Therefore, when the primary suction hole is engaged onto tissue, there is still a suction flowrate maintained by the peripheral holes—thus cooling the tip and ensuring that saline continues to flow while the main front facing hole is blocked.

The problem with prior art instruments is that legacy configurations for primary and peripheral suction are largely not feasible within an opposite sided RF shaver, as described below.

In an opposite sided RF shaver configuration, there are two possible suction flow paths. One through the shave window, and one through the RF window. It is preferable to minimise the flow through the shave window while using the RF side, and minimise flow through the RF window while using the shave function. This ensures that the maximum available saline suction pressure and flow-rate is directed through the working suction window (whether that is the RF window or the shave window). The shaver suction window can preferably be closed during RF activation, via keeping the inner blade stationary with the teeth overlapping to close the window (as illustrated in FIG. 3). It is not easily feasible to close the RF suction window during shaving, as this would require separate mechanical actuation. For this reason, it is preferable to minimise the number and size of RF windows as much as possible, so that the shave function is not greatly impeded by a lack of available suction pressure. A lack of available suction pressure can produce undesirable results such as the RF tip overheating and/or bad visibility of the surgical site (which could be due to air bubbles and/or tissue debris). Returning to the prior art example cited above (WO 2009/019426), it is clear that the peripheral suction path of this disclosure increases the surface area of the RF windows, such that the available suction pressure would be significantly decreased. If the arrangement of WO 2009/019426 was applied to an opposite sided RF shaver, the shave function would be impeded by the lack of available suction pressure in the ways described above.

Another problem in an opposite sided RF shaver, is controlling the preferential RF tracking distance to ensure that the intended RF effect on tissue occurs on the outside face of the tip between the active RF electrode and the preferential return path also on the outside of the distal tip surface. In one configuration, the inner blade also forms part of the return assembly, as it is in close contact with the outer shaft which is used as a return path. Therefore, a configuration is required which ensures that a significant amount of RF energy does not pass from the active tip, internally through the suction holes, and uses the inner blade or inner surfaces of outer blade as a primary return path, as this could cause plasma to be generated within the distal tip assembly. This plasma would form no useful purpose, and negatively impact the RF efficiency of the device. It may also cause unintended heating and overall degradation of the tip, including the inner blade edges which could also impact shaving performance. As described above, the peripheral suction channel (25) of WO 2009/019426 is a gap between the insulating member and the active electrode, and provides a direct path to the suction lumen (22), without going via the primary suction channel connecting the primary suction aperture (14a) to the suction lumen (22). This would result in RF energy passing from the active tip to the inner blade via the gap (25).

A configuration is required which offers the opportunity for peripheral suction, while not negatively affecting the shave performance via a loss of suction, or compromising the internal tracking distances.

SUMMARY OF THE INVENTION

Embodiments of the present invention provide a solution to the problems discussed above by providing an end effector for an electrosurgical instrument with peripheral suction inlets, without substantially reducing the suction pressure being delivered to the active electrode. Embodiments of the present invention achieve this by creating additional (peripheral) fluid channels which provide alternative access points to the primary fluid channel. The peripheral suction inlets do not have independent fluid channels connecting to the lumen, but instead have small fluid channels which bypass the primary suction aperture but connect to the primary fluid channel. In use, if the primary suction aperture should become blocked, the peripheral suction inlets can be used to provide suction to the end effector. Further, the embodiments described herein are shaped and located so as not to provide a shorter RF path from the active tip to the inner blade—which would result in unwanted plasma within the distal tip assembly. The end effector is capable of different operations, including mechanical cutting of tissue, and electrosurgical ablation, sealing and/or coagulation of tissue.

In an embodiment of the invention, recesses are created in a retainer which is joined to the active tip in order to keep the tip and retainer in place within the insulating material. The recesses are cut-outs in the bottom of the retainer. The recesses allow fluid to flow underneath the active tip and retainer and into the primary suction channel, bypassing the primary suction aperture.

In a further embodiment of the invention, recesses are created where the retainer and the active tip meet. The recesses allow fluid to flow through the active tip/retainer components and into the primary suction channel, bypassing the primary suction aperture.

In a further embodiment of the invention, recesses are created in the active tip component. The recesses allow fluid to flow straight through the active tip and into the primary suction channel, bypassing the primary suction aperture.

In a further embodiment of the invention, recesses are created in the retainer component. The recesses allow fluid to flow through the retainer and into the primary suction channel, bypassing the primary suction aperture.

In a further embodiment of the invention, recesses are created in the part of the insulating material where the active tip/retainer components are held. The recesses allow fluid to flow beneath the active tip and the retainer and into the primary suction channel, bypassing the primary suction aperture. In this embodiment, no recesses are required in either of the retainer component or the active tip.

Any of the additional fluid channels of the above described embodiments could be arranged around the primary suction aperture so as to receive fluid from any number of directions in use.

In view of the above, from one aspect the present invention provides an end effector for an electrosurgical instrument, comprising: an active electrode received by an insulating material, the active electrode comprising a primary suction aperture which provides access to a primary fluid (suction) channel extending from the active electrode, through the insulating material, to a lumen, the lumen being arranged to carry fluid to and from a surgical site when in use; and at least one additional fluid channel providing alternative access to the primary fluid channel from the active electrode, wherein the at least one additional fluid channel bypasses the primary suction aperture.

Such an arrangement improves upon the known RF shaver arrangements of the prior art by providing alternative suction inlets to the primary suction inlet, which may become blocked in use, without substantially reducing the suction pressure or providing a shorter RF path from the active tip to the return electrode via the suction hole. The return electrode may be the inner blade or inner surfaces of the outer blade component.

The active electrode may be received in a recess of the insulating material. This is advantageous as the active electrode and the insulating material can be formed so as to fit such that the active electrode is securely held in the recess of the insulating material. This is achieved by fixing the active electrode and the retainer component with a joining process (e.g. laser weld) to create an interlock within the insulator.

The at least one additional fluid channel may connect to the primary fluid channel between the active electrode and the insulating material. This is advantageous as this is a convenient location for the additional fluid channel to connect to the primary fluid channel while bypassing the primary fluid aperture. As this connection point is near the top of the primary suction channel, the additional fluid channels do not create a shorter RF path from the active electrode to the return electrode. If the connection point were further down the primary suction channel, this could create a shorter RF path between the active electrode and the return electrode which would be undesirable for reasons outlined above.

The active electrode may have recesses to form part of the at least one additional fluid channel. Part of the at least one additional fluid channel may flow through the active electrode.

The insulating material may have recesses to form part of the at least one additional fluid channel. This may be advantageous if having recesses in the active electrode and/or any retainer component is undesirable.

The end effector may further comprise a retainer to hold the active electrode in place. This is advantageous as a retainer component can increase the security of the active electrode being held within the insulating material. The retainer may have recesses to form part of the at least one additional fluid channel. This may be advantageous if having recesses in the active electrode and/or the insulating material is undesirable. Part of the at least one additional fluid channel may flow through the retainer. The recesses of the retainer may be formed in the base of the retainer. Part of the at least one additional fluid channel may flow beneath both the active electrode and the retainer. Part of the at least one additional fluid channel may flow between the retainer and the insulating material.

Both the active electrode and the retainer may have recesses to form part of the at least one additional fluid channel. Part of the at least one additional fluid channel may flow between the retainer and the active electrode.

The end effector may comprise a plurality of additional fluid channels. This is advantageous as if the primary suction aperture and an aperture to one additional fluid channel were to become blocked, there would be a further aperture to a further additional fluid channel available. Having more options for suction inlets is advantageous as suction can cool the RF tip by drawing colder saline over the hot RF tip during use, help to remove ablated tissue debris from surgical site, remove bubbles to improve joint visibility; and have a positive effect on the formation of plasma at the tip.

The end effector may further comprise a rotary shaver arrangement. The rotary shaver arrangement may comprise an inner rotatable shaver blade, concentrically surrounded by an outer shaft.

The lumen may be defined by an inner rotatable shaver blade, concentrically surrounded by an outer shaft acting as a return electrode.

The surface of the active electrode may be approximately rectangular shaped. The active electrode may be formed from a metal, and preferably the metal may be any one of copper, stainless steel, tungsten or an alloy of tungsten and platinum. The insulating material may be formed from ceramic.

Another aspect of the present disclosure provides an electrosurgical instrument, comprising: a hand-piece; one or more user-operable buttons on the handpiece that control the instrument to operate, and an operative shaft, having RF electrical connections, and drive componentry for an end effector, the electrosurgical instrument further comprising an end effector as described above, a rotary shaver arrangement being operably connected to the drive componentry to drive the rotary shaver to operate in use, and the active electrode being connected to the RF electrical connections.

A yet further aspect provides an electrosurgical system, comprising: an RF electrosurgical generator; a suction source; and an electrosurgical instrument according as described in the above aspect, the arrangement being such that in use the RF electrosurgical generator supplies an RF coagulation or ablation signal via the RF electrical connections to the active electrode.

BRIEF DESCRIPTION OF THE DRAWINGS

Embodiments of the invention will now be further described by way of example only and with reference to the accompanying drawings, wherein like reference numerals refer to like parts, and wherein.

DETAILED DESCRIPTION OF THE EMBODIMENTS

Embodiments of the present invention involve a modification of either the tip retainer component, the active tip component, a one-piece active tip, or the ceramic component to allow saline to pass around the periphery of the tip, and through/around the tip, without creating any additional suction holes through the ceramic which would violate the internal RF tracking distance. This solution should also not increase the overall flow-rate via any additional or larger holes than is necessary. The solutions would re-direct flow if/when the primary suction hole is blocked via contacting target tissue.

This can be achieved in the following ways:
1. Tip retainer with cut-outs in base.
2. Tip retainer or one-piece active tip or active tip alone with cut-outs at mating portion.
3. Active tip or tip retainer component with through holes.
4. Ceramic with recesses in base for fluid flow.

The above four concepts could be combined in any number of permutations which would likely be guided by suction/clogging performance on tissue, required flowrate to provide the necessary suction effect, and manufacturability constraints. The above concepts will be described below in more detail, with reference to the Figures.

Figure 1:
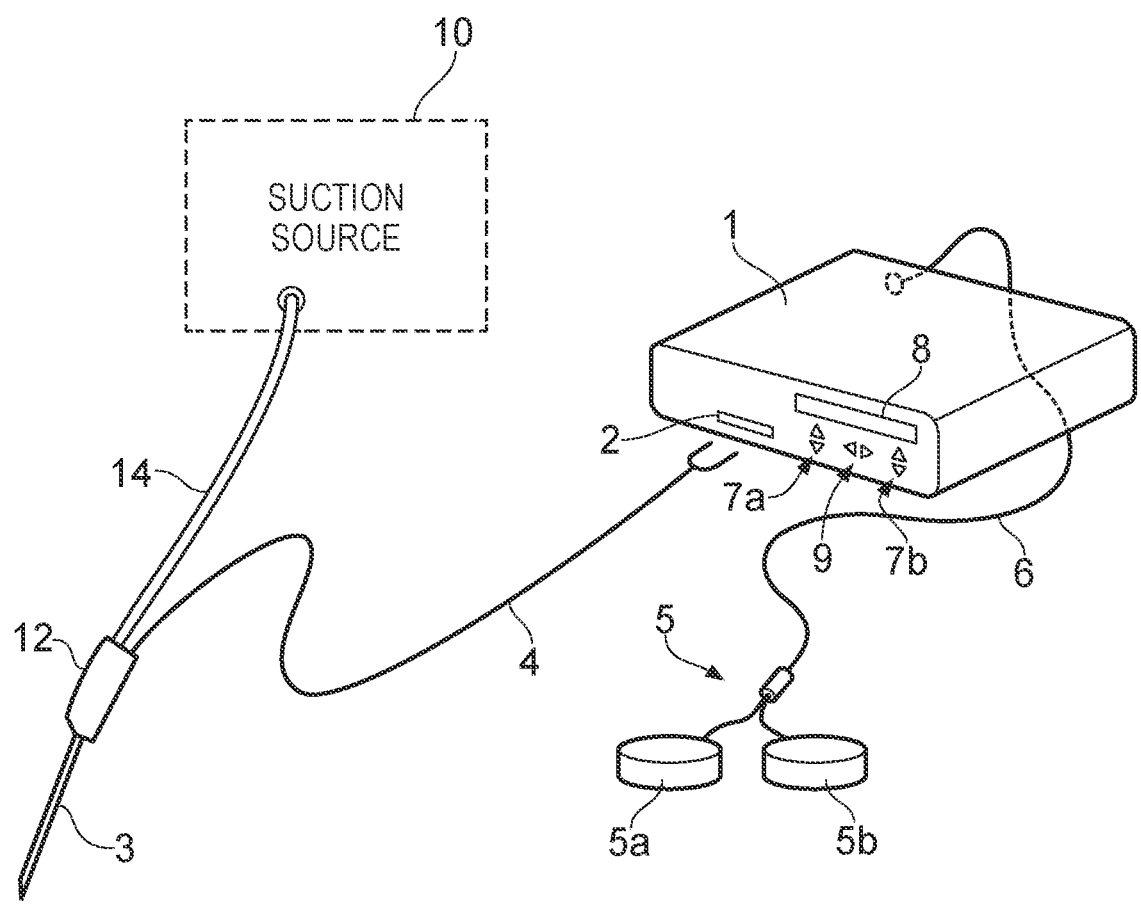
FIG. 1 is an example of the electrosurgical instrument system comprising an electrosurgical instrument according to the present invention.

FIG. 1 shows an electrosurgical apparatus including an electrosurgical generator 1 having an output socket 2 providing a radio frequency (RF) output, via a connection cord 4, for an electrosurgical instrument 3. The instrument 3 has a suction tube 14 which is connected to a suction source 10. Activation of the generator 1 may be performed from the instrument 3 via a handswitch (not shown) on the instrument 3, or by means of a footswitch unit 5 connected separately to the rear of the generator 1 by a footswitch connection cord 6. In the illustrated embodiment, the footswitch unit 5 has two footswitches 7 and 8 for selecting a coagulation mode or a cutting or vaporisation (ablation) mode of the generator 1 respectively. The generator front panel has push buttons 9 and 10 for respectively setting ablation (cutting) or coagulation power levels, which are indicated in a display 11. Push buttons 12 are provided as an alternative means for selection between the ablation (cutting) and coagulation modes.

Figure 2:
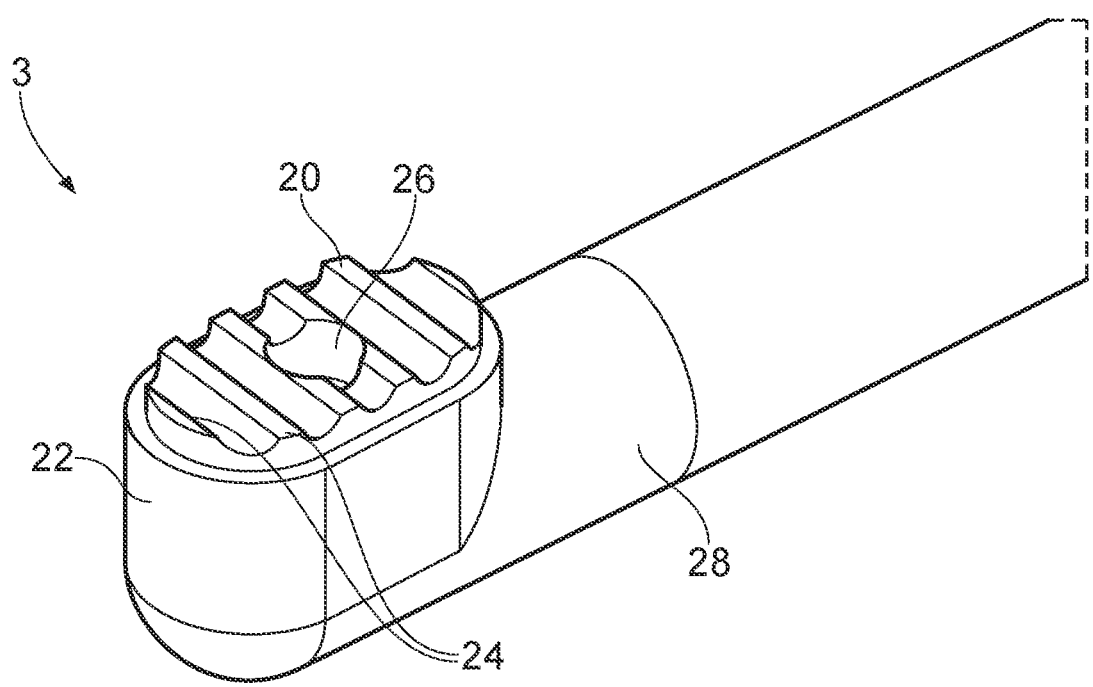
FIG. 2 is an example of an RF electrosurgical instrument.

FIG. 2 shows an example of an RF side of an electrosurgical instrument 3 in more detail. The RF side of the electrosurgical instrument 3 comprises an electrode assembly comprising an active electrode for tissue treatment ("active tip") 20 received in a ceramic insulator 22. The active tip 20 is provided with projections 24 to concentrate the electric field at those locations. The projections 24 also serve to create a small separation between the planar surface of the active electrode 20 and the tissue to be treated. This allows conductive fluid to circulate over the planar surface, and avoids overheating of the electrode or the tissue. The active tip 20 of the instrument is provided with a primary suction aperture 26, which is the opening to a primary fluid channel (not shown) extending to a lumen (not shown) within an outer shaft 28 which may act as a return electrode. The lumen connects the suction aperture 26 to the suction pump 10 to transport fluids from the active tip 20 to the pump 10. The lumen also constitutes means for electrically connecting the active electrode 20 to the generator 1. The opposite shaver side of the electrosurgical instrument is not shown in FIG. 2.

The electrically conductive material may be any material suitable for forming an active electrode tip 20, for example, a metal such as copper or a stainless steel, tungsten or an alloy of tungsten and platinum.

Figure 3:
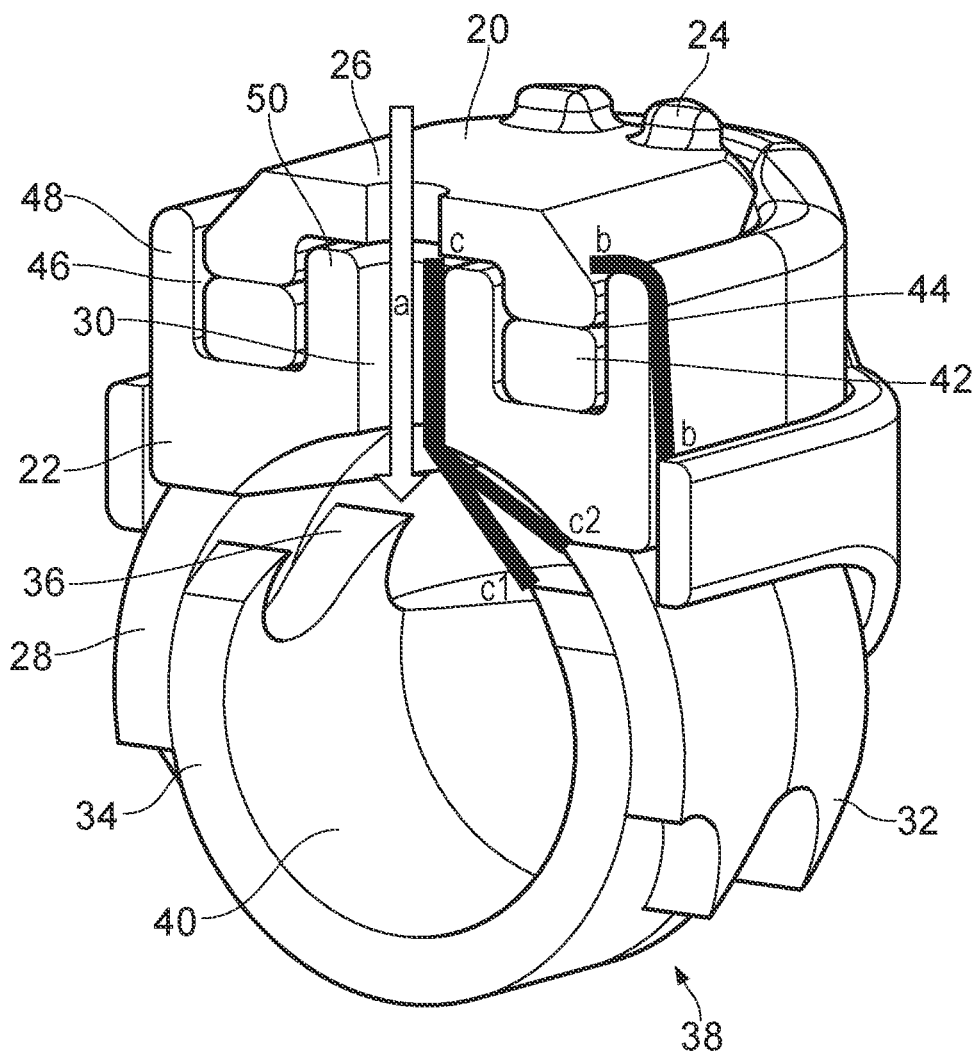
FIG. 3 is a cross-sectional perspective diagram of the state of the art design of an opposite sided RF shaver (without peripheral suction)

FIG. 3 shows a cross section of an opposite sided RF shaver electrosurgical instrument 3, without the peripheral suction of the present invention. The line bb indicates the shorter preferential RF tracking path. The line cc1 indicates the longer, unintended tracking path through the primary suction channel 30 to inner blade edge. The line cc2 indicates the longer, unintended tracking path through the primary suction channel 30 to the outer blade 32. The outer blade 32 is the primary return path, while the inner blade 34 is a coincidental return by virtue of being in close contact with the outer blade. In some examples, the inner blade could be made from an insulated material (e.g. insulated steel, or fully ceramic), in this case, the inner blade 34 would not act as a return path. The arrow a indicates the saline suction path during RF use (i.e. through the primary suction channel 30). The electrosurgical instrument 3 comprises an outer shaft 28 which acts as a return electrode, the outer shaft 28 having cutting teeth 32. The instrument also comprises an inner shaver blade 34 having cutting teeth 36. The outer shaft 28 and the inner shaft 34 are concentrically arranged such that the cutting teeth 32, 36 frame a cutting window 38. When the shaver component (i.e. the inner and outer blades) is in use, the inner shaver blade 34 rotates such that the inner 36 and outer 32 teeth cut tissue. In FIG. 3, the shaver component is not in use, and the cutting window 38 is closed. The inner shaver blade 34 defines the lumen 40 which carries fluid from the active tip 20. Connected to the outer shaft is an insulating component 22 which insulates the active tip 20 from the outer shaft return path 28. The insulating material 22 may be, for example, a ceramic material such as alumina, zirconia toughened alumina (ZTA), yttria stabilized zirconia (YTZP) or the like. The active tip 20 may be held in place by a retainer 42 (as shown in FIG. 3). Where the retainer 42 and the active tip 20 meet is referred to as the mating portion 44. Alternatively, the active tip 20 and retainer 42 may be formed as a single component (a "one-piece tip"). The primary suction channel 30 extends from the surface of the active tip 20 through the active tip 20 and the insulating material 22 to the lumen 40. The opening of the primary suction channel 26 is located on the surface of the active tip 20 ("the primary suction aperture"). The primary suction aperture 26 may be located in the centre of the active tip 20, or offset to one side. The insulating material 22 comprises a recess 46 where the retainer 42 is positioned. The recess 46 is defined by outer 48 and inner 50 lips. On top of the retainer 42, the active tip 20 is held in place such that the active tip 20 extends above the outer lips 48 of the insulating material 22. In the case of a one-piece tip, the active tip 20 is positioned directly into the recess 46 of the insulting material 22. The primary suction channel 30 runs between the two inner lips 50 from the primary suction aperture 26 directly down to the lumen 40. The lumen 40 is connected to the suction source 10 via suction tubes 14 (as shown in FIG. 1).

In embodiments of the present invention described herein, an additional (peripheral) fluid flow channel runs down into the recess 46 in the insulating material 22 (between the outer lips 48 of the insulating material 22 and the active tip 20/retainer 42), beneath or through the retainer 42/active tip 20, and out of the recess 46 (between the inner lips 50 of the insulating material 22 and the active tip 20/retainer 42). At this point, the additional fluid flow channel connects with the primary suction channel 30, and so fluid can then flow down to the lumen 40 via the primary suction channel 30.

FIGS. 4-7 described below illustrate embodiments of the present invention which are similar to the above described FIG. 3, but show variations relating to the additional fluid flow channel.

Figure 4:
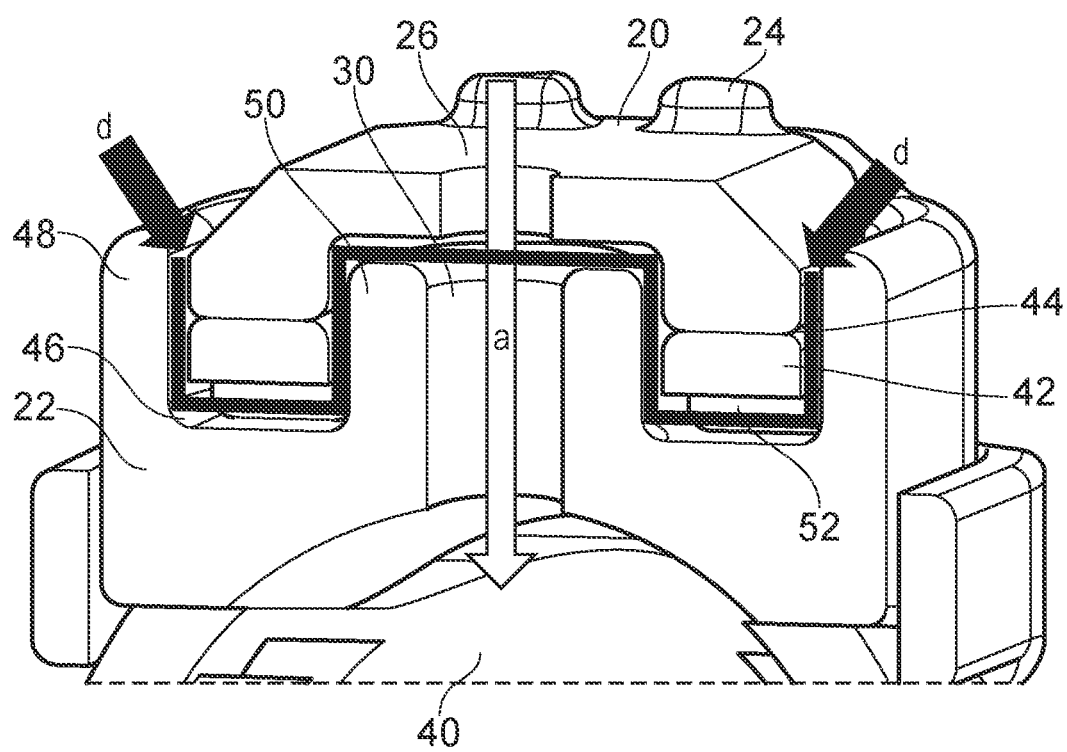
FIG. 4 is a cross-sectional diagram illustrating an apparatus according to the present invention wherein the tip retainer has cut-outs in the base.

FIG. 4 shows a cross-section of one embodiment according to the present invention wherein the tip retainer 42 has recesses 52 in the base which would allow an additional fluid flow pathway d between the retainer 42 and the insulating material 22.

In FIG. 4, the active tip 20 is held in place within the insulating material 22 by a retainer 42. The retainer 42 has cut-outs 52 (or "recesses") in its base, providing space between the retainer 42 and the insulating material 22 for the additional fluid flow channel d to run beneath the retainer 42/active tip 20 components. This allows fluid to flow from the outer edge of the active tip 20, beneath the active tip 20 and the retainer 42 (but above the insulating material 22), and up to join the primary suction channel 30 which is connected to the lumen 40, bypassing the primary suction aperture 26.

Figure 5:
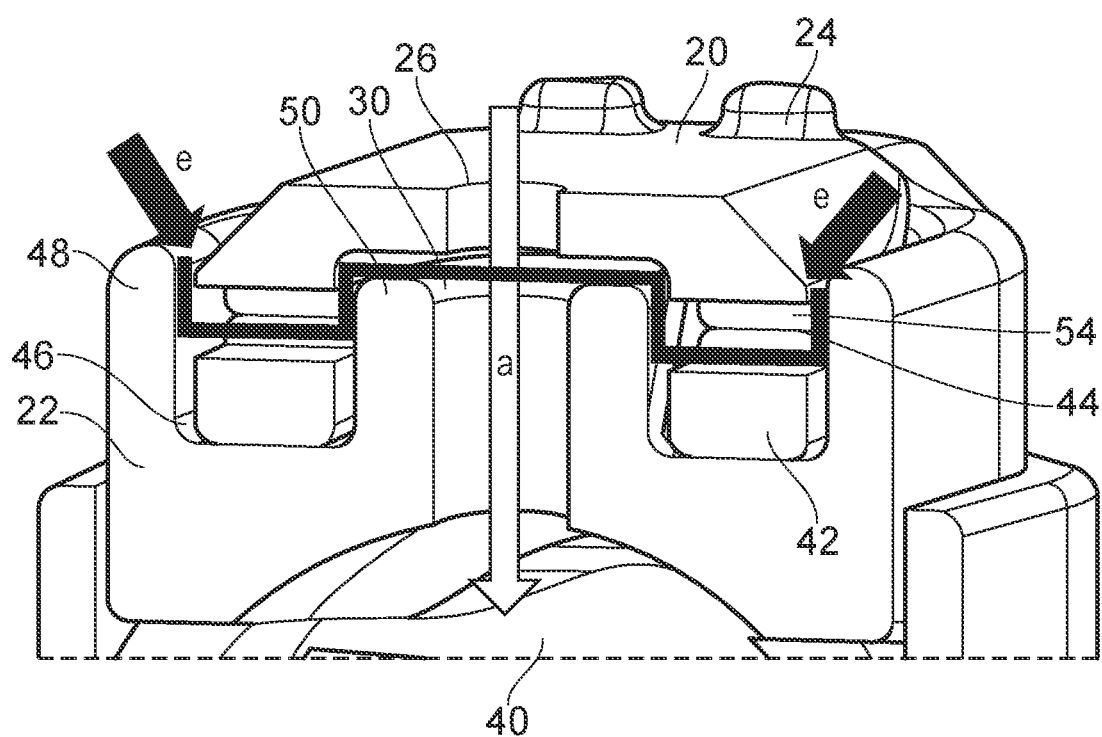
FIG. 5 is a cross-sectional diagram illustrating an apparatus according to the present invention wherein the tip retainer and/or the active tip have cut-outs at the mating portion.

FIG. 5 shows a cross-section of one embodiment according to the present invention wherein both the tip retainer 42 (as described above in relation to FIG. 4) and the active tip 20 have recesses 54 where they meet (i.e. at the 'mating portion' 44). This allows a fluid flow pathway e between the retainer 42 and the active tip 20. Alternatively, the recesses 54 could be formed only in the tip retainer 42, or only in the active tip 20.

In FIG. 5, the retainer 42 is used to hold the active tip 20 in place. Where the retainer 42 connects with the active tip 20 is known as the mating portion 44. Cut-outs 54 (or recesses) to provide space for the additional fluid flow channel e are positioned at this mating portion 44. This allows the additional fluid flow channel e to run down into the recess 46 in the insulating material 22 (between the outer lips 48 of the insulating material 22 and the active tip 20/retainer 42), between the retainer 42 and the active tip 20 (using the cut-outs 54 at the mating portion 44), and out of the recess 46 (between the inner lips 50 of the insulating material 22 and the active tip 20/retainer 42). At this point, the additional fluid flow channel e connects with the primary suction channel 30, and so fluid can then flow down to the lumen 40 via the primary suction channel 30, bypassing the primary suction aperture 26.

Alternatively, the cut-outs 54 could be formed above the mating portion 44, i.e. only in the active tip 20 component. This would result in a shallower-shaped additional fluid flow channel e, i.e. the additional fluid flow channel e would not extend so deeply into the insulating material 22.

Alternatively, the cut-outs 54 could be formed below the mating portion 44, i.e. only in the retainer 42 component. This would result in a deeper-shaped additional fluid flow channel e, i.e. the additional fluid flow channel e would extend further into the insulating material 22.

From FIG. 5 it is also clear how a similar fluid flow pathway could be formed in the case of a one-piece tip design (i.e. where the tip retainer 42 and the active tip 20 are one component). The recesses 54 could be created in the same locations as in FIG. 5, but with one tip component rather than two. In this case, the active tip 20 would not be held in place using a retainer 42, and instead would just be a one-piece active tip 20 sat within the recess 46 of the insulating material 22, the cut-outs 54 could be formed in the one-piece active tip 20 so as to give the same shaped additional fluid flow channels e as described above.

Figure 6:
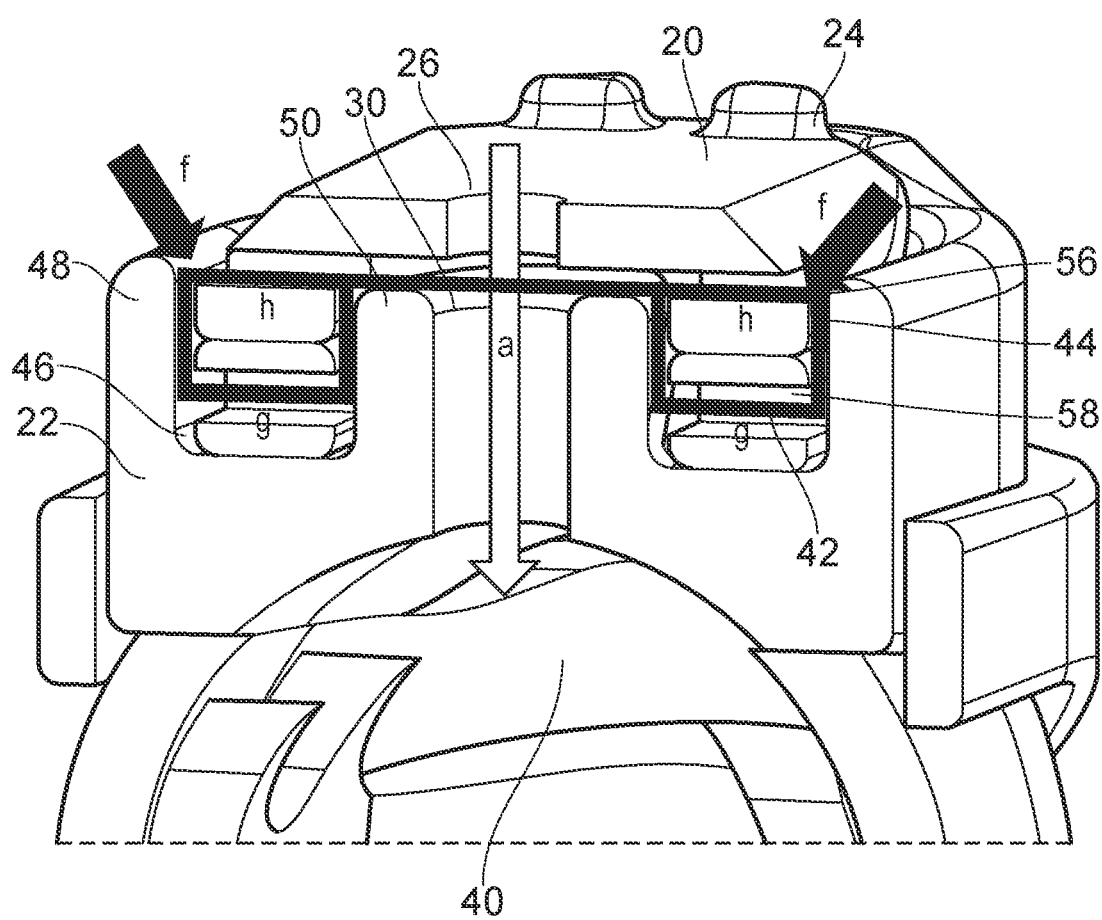
FIG. 6 is a cross-sectional diagram illustrating an apparatus according to the present invention wherein the active tip and/or the tip retainer component have through holes (holes in both shown)

FIG. 6 shows a cross-section of one embodiment according to the present invention wherein the active tip 20 or the tip retainer 42 component has through holes. FIG. 6 shows two options at once. The first option is recesses 56 in the active tip 20. This results in a flow path fh running directly through the active tip 20 to the primary suction channel 30 (flow indicated by arrow a). In this case, the additional fluid flow channel fh does not extend down into the recess 46 in the insulating material 22, as in the previously described embodiments. The primary suction aperture 26 is located on the surface of the active tip 20. The additional fluid flow suction channel fh runs through the active tip 20 and meets the primary suction channel 30 directly below the primary suction aperture 26. As described above, the additional fluid flow channel fh connects with the primary suction channel 30, bypassing the primary suction aperture 26, and so fluid can then flow down to the lumen 40 via the primary suction channel 30.

The second option shown in FIG. 6 is having recesses 58 in the tip retainer 42. This results in the fluid flow pathway fg running down into the recess 46 in the insulating material 22 (between the outer lips 48 of the insulating material 22 and the active tip 20/retainer 42), through cut-outs 58 in the retainer 42, and out of the recess 46 (between the inner lips 50 of the insulating material 22 and the active tip 20/retainer 46). At this point, the additional fluid flow channel fg connects with the primary suction channel 30, again, bypassing the primary suction aperture 26, and so fluid can then flow down to the lumen 40 via the primary suction channel 30.

Figure 7:
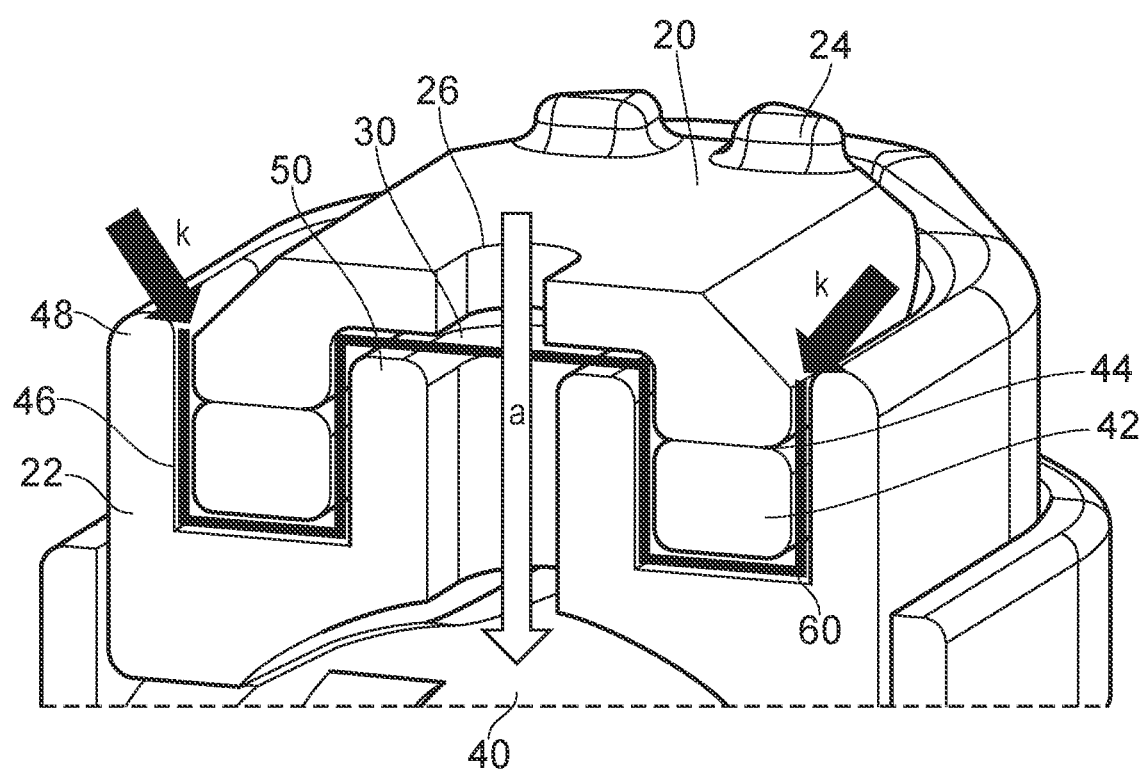
FIG. 7 is a cross-sectional diagram illustrating an apparatus according to the present invention wherein the ceramic has recesses in base for fluid flow.

FIG. 7 shows a cross-section of one embodiment according to the present invention wherein the insulating material 22 has recesses 60 in its base for fluid flow. Recesses 60 could be created in the insulating material 22 to allow saline to flow underneath either the tip retainer 42 or a one-piece tip design, to the primary suction channel 30. In this embodiment, the active tip 20 and retainer 42 (or a one-piece active tip) are formed as normal, without any recesses. Instead, in the recess 46 of the insulating material 22 where the retainer 42/active tip 20 is held, further recesses 60 are created in the base to form part of the additional fluid flow channel k beneath the active tip 20/retainer 42. This allows the additional fluid flow channel k to run down into the recess 46 in the insulating material 22 (between the outer lips 48 of the insulating material 22 and the active tip 20/retainer 42), beneath the retainer 42/active tip 20 (using the further recesses 60 in the insulating material 22), and out of the recess 46 (between the inner lips 50 of the insulating material 22 and the active tip 20/retainer 42). At this point, the additional fluid flow channel k connects with the primary suction channel 30, and so fluid can then flow down to the lumen 40 via the primary suction channel 30, bypassing the primary suction aperture 26.

Figure 8:
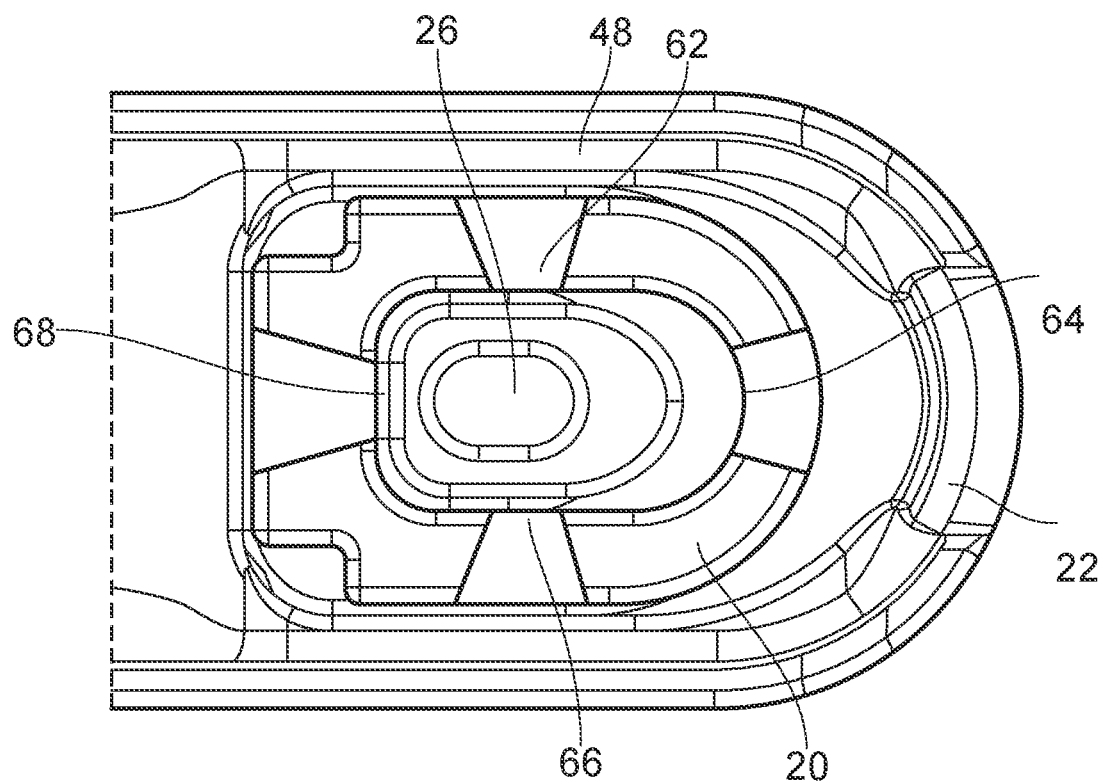
FIG. 8 is a plan view illustrating an apparatus according to the present invention, in this example, the embodiment also illustrated in FIG. 4 is shown.

FIG. 8 illustrates how each of the above embodiments could be spaced about the primary suction aperture 26 in a number of ways which are not visible in FIGS. 4-7. FIG. 8 shows a configuration showing four peripheral suction channel pathways 62, 64, 66, 68 in accordance with the embodiment shown in FIG. 4. This configuration could also apply to any of the embodiments described above. Any number of pathways could be created. The final number would depend on practicality and necessity. In FIG. 7, four additional channels 62, 64, 66, 68 are located around the primary suction aperture 26/channel 30. The additional channels 62, 64, 66, 68 are equidistantly spaced out from the primary suction channel 30, such that there is one additional channel 64 in front of the primary channel 30, one 68 behind, one to the left 62 and one to the right 66. The location and number of additional channels could obviously be varied to suit individual instruments. It is also clear from FIG. 8 that the additional channels 62, 64, 66, 68 bypass the primary suction aperture 26. Any of the additional fluid channels d, e, fh, fg, or k described above could be arranged in any combination as the additional fluid channels, 62, 64, 66, 68.

As mentioned above, the embodiments illustrated in FIGS. 4-7 could be combined in any number of permutations which would likely be guided by suction/clogging performance on tissue, required flowrate to provide the necessary suction effect, and manufacturability constraints.

Various further modifications to the above described embodiments, whether by way of addition, deletion or substitution, will be apparent to the skilled person to provide additional embodiments, any and all of which are intended to be encompassed by the appended claims.

The invention claimed is:

1. An end effector for an electrosurgical instrument, comprising:
   an active electrode received by an insulating material, the active electrode comprising a primary suction aperture which provides access to a primary fluid channel extending from the active electrode, through the insulating material, to a lumen, the lumen being arranged to carry fluid from a surgical site when in use;
   at least one additional fluid channel providing alternative access to the primary fluid channel from the active electrode, the at least one additional fluid channel bypassing the primary suction aperture; and
   a retainer to hold the active electrode in place, the retainer including recesses to form part of the at least one additional fluid channel.

2. The end effector according to claim 1, wherein the active electrode is received in a recess of the insulating material.

3. The end effector according to claim 1, wherein the at least one additional fluid channel connects to the primary fluid channel between the active electrode and the insulating material.

4. The end effector according to claim 1, wherein the active electrode has recesses to form part of the at least one additional fluid channel.

5. The end effector according to claim 1, wherein part of the at least one additional fluid channel flows through the active electrode.

6. The end effector according to claim 1, wherein the insulating material has recesses to form part of the at least one additional fluid channel.

7. The end effector according to claim 1, wherein part of the at least one additional fluid channel flows through the retainer.

8. The end effector according to claim 1, wherein the recesses of the retainer are formed in a base of the retainer.

9. The end effector according to claim 1, wherein part of the at least one additional fluid channel flows beneath both the active electrode and the retainer.

10. The end effector according to claim 1, wherein part of the at least one additional fluid channel flows between the retainer and the insulating material.

11. The end effector according to claim 1, wherein both the active electrode and the retainer have recesses to form part of the at least one additional fluid channel.

12. The end effector according to claim 1, wherein part of the at least one additional fluid channel flows between the retainer and the active electrode.

13. The end effector according to claim 1, comprising a plurality of additional fluid channels.

14. The end effector according to claim 1, further comprising a rotary shaver arrangement.

15. The end effector according to claim 1, wherein the lumen is defined by an inner rotatable shaver blade, concentrically surrounded by an outer shaft acting as a return electrode.

16. The end effector according to claim 1, wherein the active electrode is formed from a metal.

17. The end effector according to claim 1, wherein the insulating material is formed from ceramic.

18. The end effector according to claim 16, wherein the metal is any one of copper, stainless steel, tungsten, or an alloy of tungsten and platinum.

19. An electrosurgical instrument, comprising:
a hand-piece;
an end effector;
one or more user-operable buttons on the hand-piece that are configured to control the instrument to operate, and
an operative shaft, having RF electrical connections, and drive componentry for the end effector;
wherein the end effector comprises:
   an active electrode received by an insulating material, the active electrode being connected to the RF electrical connections, and comprising a primary suction aperture which provides access to a primary fluid channel extending from the active electrode, through the insulating material, to a lumen, the lumen being arranged to carry fluid from a surgical site when in use;
   at least one additional fluid channel providing alternative access to the primary fluid channel from the active electrode, the at least one additional fluid channel bypassing the primary suction aperture; and
   a retainer to hold the active electrode in place, the retainer including recesses to form part of the at least one additional fluid channel.

20. An electrosurgical system, comprising:
an RF electrosurgical generator;
a suction source; and
an electrosurgical instrument, comprising:
   a hand-piece;
   an end effector;
   one or more user-operable buttons on the hand-piece that are configured to control the instrument to operate, and
   an operative shaft, having RF electrical connections, and drive componentry for the end effector;
wherein:
   the end effector comprises:
      an active electrode received by an insulating material, the active electrode being connected to the RF electrical connections, and comprising a primary suction aperture which provides access to a primary fluid channel extending from the active electrode, through the insulating material, to a lumen, the lumen being arranged to carry fluid from a surgical site when in use;
      at least one additional fluid channel providing alternative access to the primary fluid channel from the active electrode, the at least one additional fluid channel bypassing the primary suction aperture; and
      a retainer to hold the active electrode in place, the retainer including recesses to form part of the at least one additional fluid channel; and
   the arrangement of the electrosurgical system is such that in use the RF electrosurgical generator supplies an RF coagulation or ablation signal via the RF electrical connections to the active electrode.

* * * * *